(12) United States Patent
Kourtakis

(10) Patent No.: US 6,413,903 B1
(45) Date of Patent: Jul. 2, 2002

(54) HIGH SURFACE AREA SOL-GEL ROUTE PREPARED OXIDATION CATALYSTS

(75) Inventor: Kostantinos Kourtakis, Swedesboro, NJ (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/786,170

(22) PCT Filed: Aug. 25, 1999

(86) PCT No.: PCT/US99/19612

§ 371 (c)(1), (2), (4) Date: Feb. 28, 2001

(87) PCT Pub. No.: WO00/12208

PCT Pub. Date: Mar. 9, 2000

Related U.S. Application Data

(60) Provisional application No. 60/098,513, filed on Aug. 31, 1998.

(51) Int. Cl.⁷ ............ B01J 27/198; C07D 307/60; C07D 307/36

(52) U.S. Cl. ............ 502/209; 502/234; 502/247; 502/350; 502/353; 549/258; 549/259; 549/260; 549/505

(58) Field of Search .............. 502/209, 234, 502/247, 350, 353; 549/258, 259, 260, 505

(56) References Cited

PUBLICATIONS

Lopez et al, Material Letters, vol. 22, p. 259–263 (1995).*
Chem Abstracts, 105:193304 (1986); Abstract of Ropa Uhlie vol. 28 (6), p. 337–339 (1986).*

* cited by examiner

*Primary Examiner*—Bernard Dentz

(57) ABSTRACT

This invention relates to catalysts useful in the vapor phase oxidation of hydrocarbons, such as 1,3-butadiene to furan and maleic anhydride. The catalysts comprise vanadium oxides, vanadium phosphorus oxides or vanadium antimony oxides incorporated in a matrix comprising oxides or oxyhydroxides of silicon, titanium, tantalum and/or niobium derived using sol-gel chemistry, optionally in the presence of an organic directing agent, such as dodecylamine.

4 Claims, No Drawings

HIGH SURFACE AREA SOL-GEL ROUTE PREPARED OXIDATION CATALYSTS

This application is a 371 of PCT/US99/19612 filed Aug. 25, 1999 which claims benefit of Provisional Application No. 60/098,513 filed Aug. 31, 1998.

FIELD OF THE INVENTION

This invention relates to catalysts useful in the oxidation of hydrocarbons. for example butadiene. The catalysts comprise vanadium oxides incorporated in a matrix comprising oxides and oxyhydroxides of silicon, titanium, tantalum and/or niobium derived using sol gel chemistry.

TECHNICAL BACKGROUND

This invention relates to a catalyst comprising vanadium oxides incorporated in a matrix comprising oxides and oxyhydroxides of silicon, titanium. tantalum and/or niobium derived using sol gel chemistry, optionally in the presence of an organic directing agent. This invention also relates to a process for the preparion of furan and maleic anhydride, more specifically, to a method for preparing furan and maleic anhydride by a vapor-phase catalytic oxidation reaction from 1,3 butadiene.

Furan is used as a chemical building block for the production of other industrial chemicals such as tetrahydrofuran, pyrrole and thiophene. Maleic anhydride can be used to manufacture tetrahydrofuran, polyester resins, fumaric and tartaric acids, pesticides, preservatives and other industrial products.

E. I. Ko, in the Handbook of Heterogeneous Catalysis, ed. by G. Ertl et al, Vol. 1. 2.1.4 (1997) reviews generally the use of sol-gel processes for the preparation of catalytic materials. There is no disclosure of or suggestion of vanadium oxides, vanadium phosphorus oxides, or vanadium antimony oxides dispersed in and distributed throughout high surface area oxides of silicon and/or titanium as being useful catalysts for the oxidation of butadiene.

Japanese Patent Application SHO 46-22009 discloses the preparation of catalysts comprising oxides of molybdenum, bismuth and vanadium in a silica matrix and their utility in the oxidation of butadiene.

U.S. Pat. No. 4,622,310 discloses inorganic phosphate aerogels. The utility disclosed is as porous inert carrier materials (supports) in polymerization and copolymerization processes. Use of the inorganic phosphates as supports in hydrocarbon oxidation processes wherein the catalyst species is $V_2O_5$, $MoO_3$, Ag. Cu, $PCl_3$ and $BiO_{23}$ (sic. $Bi_2O_3$ is meant) are described. There is no disclosure nor suggestion of incorporating the catalytic material within the inorganic phosphate gel matrix.

U.S. Pat. No. 5,264,203 describes the preparation of large pore crystalline materials, for example silicoaluminophosphates, optionally comprising a metal, by use of an organic directing agent.

SUMMARY OF THE INVENTION

This invention provides compositions comprising catalytic species selected from the group consisting of vanadium oxides, vanadium phosphorous oxides and vanadium antimony oxides incorporated in a matrix material selected from the group of oxides and oxyhydroxides of silicon, titanium, tantalum and niobium, which compositions are prepared by sol gel chemistry, optionally in the presence of an organic directing agent.

This invention further provides an improved process for the oxidation of butadiene to furan and maleic anhydride, the improvement comprising the use of a composition comprising catalytic species selected from the group consisting of vanadium oxides, vanadium phosphorous oxides and vanadium antimony oxides incorporated in a matrix material selected from the group of oxides and oxyhydroxides of silicon, titanium, tantalum and niobium, which compositions are prepared by sol gel chemistry, optionally in the presence of an organic directing agent.

DETAILED DESCRIPTION OF THE INVENTION

Catalysts that are highly reactive for the oxidation of butadiene were synthesized by incorporating catalyst species into matrices containing silicon, titanium, tantalum and niobium oxides and oxyhydroxides to generate high surface area catalysts. Specific catalytic species employed include vanadium oxides, vanadium phosphorus oxides, and vanadium antimony oxides. Bar matrix is meant a skeletal framework of oxides and oxyhydroxides which can be derived from the hydrolysis of alkoxides and other reagents.

The catalysts of the present invention may be prepared by various methods. A non-aqueous solution containing the catalyst species and matrix precursors (generally, but not necessarily, alkoxides) is added to solution containing water, acid or base, alcohol and, optionally, an organic directing agent to form a catalyst precursor gel or gelatinous material and subsequently drying the gel. Alternatively, a solution containing water, acid or base and alcohol is added to a nonaqueous solution containing catalyst species, matrix precursors, and, optionally, an organic directing agent. In general, the optional organic directing agent can be in the aqueous or non-aqueous solutions. The catalytically active species can be in the aqueous or non-aqueous solutions. The order can be (i) aqueous solutions added to non-aqueous solutions, or (ii) non-aqueous solutions added to aqueous solutions.

The inorganic metal alkoxides used in this invention, i.e. the alkoxides of silicon, titanium, tantalum and niobium may include any alkoxide which contains from 1 to 20 carbon atoms and preferably 1 to 5 carbon atoms in the alkoxide group, which are preferably soluble in the liquid reaction medium. In this invention, preferably, C1–C4 systems, ethoxides, isopropoxides or n-butoxides are used.

One of the criteria for the starting material are inorganic alkoxides or metal salts which will dissolve in the specified medium or solvent. Commercially available alkoxides can be used. However, inorganic alkoxides can be prepared by other routes. Some examples include direct reaction of zero valent metals with alcohols in the presence of a catalyst. Many alkoxides can be formed by reaction of metal halides with alcohols. Alkoxy derivatives can be synthesized by the reaction of the alkoxide with alcohol in a liqand interchange reaction. Direct reactions of dialkylamideg with acohol also form alkoxide derivatives.

The catalytic species, i.e., the vanadium oxides, vanadium phosphorous oxides and vanadium antimony oxides are derived from soluble alkoxides or salts. Preferred species include $NH_4VO_3$, vanadium trisisopropoxide, and antimony (III) n-butoxide (Sb $(OC_4H_9)_3$.

The organic direct agent, if present, is selected from the group consisting aliphatic amines, aromatic amines, cyclic aliphatic amines, polycyclic aliphatic amines and an amonium or phosphonium ion. A preferred organic directing agent is dodecylamine.

After combining the solutions employed, the alkoxides will react and polymerize to form a gel. As polymerization and crosslinking proceeds viscosity increases and the material can eventually set to a rigid "gel". The "gel" consists of a crosslinked network of the desired material which incorporates the original solvent within its open porous structure. The "gel" may then be dried, typically by either simple heating in a flow of dry air to produce an aerogel or the entrapped solvent may be removed by displacement with a supercritical fluid such as liquid $CO_2$ to produce an aerogel, as described below. Final calcination of these dried materials to elevated temperatures (>200° C.) results in products which typically have very porous structures and concomitantly high surface areas.

Depending on the alkoxide system and the water/alkoxide ratios used, a discernible gel point can be reached immediately or hours later. The molar ratio of the total water added (including water present in aqueous solutions), can vary according to the specific inorganic alkoxide being reacted. Generally, a molar ratio of water to alkoxide within the broad range of 3 to 150 is within the scope of this invention. It is understood that the order of addition of the various solutions can be reversed.

The addition of acidic or basic reagents to the gellation reaction can have an effect on the kinetics of the hydrolysis and condensation reactions, and the microstructure of the oxide/hydroxide matrices derived from the alkoxide precursor which entraps or incorporates the soluble metal reagents. Generally, a pH range of 1–12 can be used, with a pH range of 1–6 preferred for these experiments.

After reaction, the catalytic species is uniformly incorporated into the gel network. Further processing to produce the final catalytic material may include a combination of calcination cycles in various media.

The solvent in the gels can be removed in several different ways: conventional drying, freeze and vacuum drying, spray drying, or the solvent can be exchanged under supercritical conditions. Removal by vacuum drying results in the formation of a xerogel. An aerogel of the material can typically be formed by charging in a pressurized system such as an autoclave. The solvent laden gel which is formed in the practice of the invention is placed in an autoclave where it can be contacted with a fluid above its critical temperature and pressure by allowing supercritical fluid to flow the material solid and liquid until the solvent is no longer being extracted by the supercritical fluid. In performing this extraction to produce the aerogel material, various fluids can be utilized at their critical temperature and pressure. For instance, fluorochlorocarbons typified by Freon brand fluorochloromethanes and ethanes, ammonia and carbon dioxide are all suitable for this process. Typically, the extraction fluids are fluids which are gases at atmospheric conditions, so that pore collapse due to the capillary forces at the liquid/solid interface are avoided during drying. The resulting material should, in most cases, possess a higher surface area than the non-supercritically dried materials.

Prior to calcination, the compositions of the present invention may show a X-ray diffraction pattern containing low angle peaks indicating the quasi-regular arrangement of mesopores which containing the organic directing agent. This is evident for catalyst precursors described in Example 2 and Example 3 before calcination, which possess low angle lines at 2.38 degrees two theta, 2.70, 4.990, 7.175 two theta (Example 2) and 2.41 degrees, 262 degrees, 5.11 degrees, 7.20 degrees, and 7.74 degrees two theta (Example 3) indicating approximately 37 Angstrom pores. The size and shape of the organic directing agent filled pores can depend on the geometry of the organic directing agent and their agglomerates or micelles. The organic directing agent may act as a template for nucleation and growth of the organic directing agent filled mesoporougs matrix, which also contains the inorganic and active component. By mesoporous, we mean 15 angstroms to 200 angstroms in diameter. Following high temperature calcination in air, the organic directing agent is removed and crystalline order is lost. The directing agent may also be removed by chemical oxidation or other methods. Powder X-ray data was obtained using a Scintag Powder X-ray Diffractometer. with 0.01 degrees 2θ steps, 1.199 seconds per step, Kα1 Cu radiation.

It is believed that the organic directing agent, optionally present in the present invention, serves as a template for the inorganic oxide so that a large unit cell is observed in powder X-ray diffraction data before calcination of the inorganic oxide. In the case of the titanium and niobium oxides, after calcination, i.e., after the organic directing agent is removed by air oxidation, long range order is lost and the material no longer exhibits the low angle X-ray diffraction peaks indicative of the mesoporous (approximately 37 A) unit cell. In the case of the silica containing catalysts, the low angle X-ray diffraction peaks are still apparent, indicating quasi-crystalline order is maintained for the large unit cell. For the catalysts of the present invention, calcination is carried out in the temperature range 300–800° C., for a time sufficient to remove the organic directing agent, usually in the time range from 30 minutes to >48 hours.

As an example of the improved catalytic activity obtained, the apparent first order rate constant for butadiene oxidation using VPO (vanadyl pyrophosphate) catalyst is 0.4 $sec^{-1}$ (at 300° C.), compared with 3.8 $sec^{-1}$ for the sol-gel derived vanadium/silicon oxide catalyst of the present invention. The vanadium/titania and vanadium/antimony/titanium oxide systems show further activity improvements over previously known catalysts.

EXAMPLES

General Procedures

Microreactor System

An automated six-reactor system was used to enable the rapid testing of catalysts for various hydrocarbon oxidation reactions. This new reactor system contains six 10¼"x¼" Hastelloy C reactors contained in six individual furnaces. Each furnace consists of an internal aluminum cylinder, split to enable reactor entry, which, in turn, is encased in an insulating material followed by containment in a steel clamshell jacket. The aluminum core is heated by four ceramic electric heating rods imbedded in the core. Each furnace is mounted vertically with the direction of gas flow from top to bottom through the reactor. Each of the six reactors is fed by a separate 100 sccm Tylan Model 260 mass flow controller. In addition Reactors 1, 2 and 3 may be fed by separate 10 sccm Tylan Model 160 mass flow controllers. Omega PX410 pressure transducers are mounted near the entrance to each of the reactors to monitor pressure changes during a test. A manifold delivers a common gas feed for all reactors. This manifold, in turn, is fed by 5 separate mass flow controllers, depending upon the feed composition desired. Gases exiting the reactors are separately fed to an 8-stream flow-thru valve which selects the stream to undergo GC analysis. In addition, each gas stream has its own vent line coming out of the 8-streamn flow-thru valve. Each of these vent lines is connected to a common vent line exiting into the hood. All gases exiting the reactors are kept hot by electrical heating tape applied to the all exit lines. A bypass from the gas inlet manifold also connects to a port of this 8-stream flow-thru valve enabling one to sample feed gas prior to passing through the reactors.

Gas Chromatographic Analysis

A Hewlett-Packard Model 5890 gas chromatography unit containing two detectors (flame ionization and thermal conductivity) was used to analyze the effluent gases. The columns used include (1) a combination of a 10'×18" SS 60/80 mesh Molecular Sieve 13× column (used to separate $O_2$, $N_2$ and CO) and a 2'×⅛" SS 80/100 mesh Haysep R column (used to separate $H_2O$, $CO_2$ and butane) and (2) a 20 m×0.53 mm DB1 capillary column used to separate the organics. Helium is used as a carrier gas for all columns. Analyses on both column systems were carried out simultaneously using separate samples taken from two 500 microliter sample loops. A valve switching scheme was used to insure that each sample was properly analyzed. The GC was programmed to control the column temperatures in a manner such that a total analysis could be completed in 15.45 min.

The response factors for the compounds of interest in our studies were determined using two methods: (1) syringe injection of gases or liquids or (2) sample loop injections of gases.

The reactor system is controlled by a TI-545 Process Logic Controller (PLC) and monitored through a Dell (Pentium processor) Personal Computer. The PLC was programmed with fail-safe interlocks to allow unattended operation. The reactor system is also interfaced with the VANTAGE data collection system and with the MULTI-CHROME gas chromatographic analysis system. A program designed to separate the data collected for a typical test run into individual data files for each reactor was written. Programs enabling a user to input data to the PLC were also written.

Catalyst Testing Procedures

Several catalyst testing protocols were implemented in this reactor system. However, all of the protocols were variations of two basic protocols involving the feeding of lean (1.5% hydrocarbon/21% $O_2$/77.5% $N_2$) or rich (9% hydrocarbon/10% $O_2$/81% $N_2$) feeds to the reactor. The basic protocol involving the lean feed was called a Test I protocol while that involving the rich feed was called the Test II protocol. In both protocols the hydrocarbon feed was sent through a reactor at nine different contact times while maintaining the temperature at a fixed value throughout the test run. A total of 13 samples were taken during a run, four of which were feed samples.

The primary objective of these protocols was to obtain an accurate assessment of the % product selectivities, % reactant conversions and rate constants associated with a given catalyst over on-stream times that varied from ca. 8 to 64 hours.

The pseudo-first order rate constant, k, given for the disappearance of butadiene was obtained by fitting the reactor data to a classical first order rate expression:

d[butadiene]/dt=−k [butadiene]

d $(x_0-x)$/dt=−k $(x_0-x)$ where $x_0$=initial butadiene concentration and y=portion of butadiene reacted.

Integrating this experession gave the concentration of butadiene exiting the reactor as a function of contact time, t, in the reactor: [exit butadiene]=$x_0$−x=$e^{-kt}$.

In addition to describing the reaction rate of butadiene with a catalyst. the rate constant k included several other factors including the dependence of the reaction rate on oxygen concentration (which remained relatively constant under our conditions) and the concentration of catalyst active sites (also assumed constant).

In the below examples, all degrees are in Centigrade and percents are mole percents unless indicated otherwise.

Example 1

Preparation of 5 mole % V, 95 mole % $SiO_2$ (using dodecylamine as a organic directing agent)

20.78 g of TEOS (tetraethylorthosilicate. Si(OCH$_2$CH$_3$)$_4$, (Aldrich, Milwaukee, Wiss.) was added to 1.14 g of vanadium tri-isopropoxide (Alfa Aesar, #89798. Alfa Inorganics) was added to a container in an inert atmosphere drybox (VAC Atmospheres). The material was loaded into a dropping funnel. In a sepatate container, 65.32 g of $H_2O$, 5 g of dodecvlamine (ACROS, New Jersey) and 0.67 g of hydrochloric acid (EM HX0603-4. Gibbstown. N.J.) were combined. The solution containing the tetraethylorthosilicate and the vanadium alkoxide was slowly added to the aqueous solution containing the dodecylamine. A white, gelatinous material formed almost immediately. The material was dried at 300° C. in air for 8 hours, followed by calcination at 600° C. for 4 hours in air.

Catalysts were formed for microreactor evaluations by pelletizing at 20,000 psi to form small disks which were subsequently crushed and sieved. For the fixed bed reactor evaluations, −40/+60 screens were used (U.S. Sieve series). Powder XRD indicated that the material was marginally crystalline.

Example 2

Preparation of 5 mole % V, 5 mole % P in in 90 mole % titanium containing matrix using dodecvlamine as a organic directing agent 42.53 g of water was added to a dropping funnel. In one container, 0.14 g of anhydrous phosphoric acid (prepared by mixing 85.70 g of 85 wt % $H_3PO_4$, J. T. Baker, 0260-000, Phillipsburg, N.J.) and 33.20 of phosphorus pentoxide, J. T. Baker 9374-01, Phillipsburg, N.J.) was added to 4.02 g of dodecylamine (ACROS 11766-5000) and 33.29 g of ethanol (Quantum Chemical, Newark, N.J.). To this container, 0.28 g of vanadium tri-isopropoxide (Alfa, 89778), 5.50 g of titanium n-propoxide (Ti(OC$_3$H$_7$)$_4$, Aldrich, 25,308-1) were added. The aqueous solution was slowly added into the container containing the anhydrous phosphoric acid, dodecylamine, and alkoxides. Reaction was noted immediately (and slightly prior) to the liquid additions. The material was calcined at 400° C., 4 hours in air followed by 550° C. for 4 hours in air. The materials were pelletized at 20,000 psi into small disks which were subsequently granulated for the microreactor evaluations.

Example 3

Preparation of 5 mole % Sb, 5 mole % V in a titanium containing matrix 42.55 g of water was added to a dropping funnel. In one container, 0.4 g of antimony (III) n-butoxide (Sb (OC$_4$H$_9$)$_3$ was added to 4.04 g of dodecylamine (ACROS, 11766-5000) and 33.23 g of ethanol (Quantum Chemical, Newark, N.J.). To this container, 0.4 g of vanadium tri-isopropoxide (Alfa 89798) and 5.53 g of titanium n-propoxide (Ti (OC$_3$H$_7$)$_4$, Aldrich, 25,308-1) were added. The aqueous solution was slowly added to the solution/slurryn containing the dodecylamine organic directing agent and alkoxides.

Reaction was noted immediately during the liquid additions. The material was calcined at 400° C. for 4 hours in air followed by 550° C. for 4 hours in air. The materials were pelletized to 20,000 psi into small disks which were granulated on −40. +60 mesh screens for the microreactor evaluations.

Example 4

Preparation of 5 mole % V. 5 mole % P. in silica containing matrix

In one dropping funnel. 0.55 g of vanadium tri-ispropoxide (Aldrich. 25,308-1). 5.69 g of TEOS [E85947-87], 0.22 g of anhydrous phosphoric acid (prepared by mixing 26.96 of 85 Aq % $H_3PO_4$ and 9.97 of phosphorus pentoxide) were combined. Into a second container, 5.62 g of dodecylamine (ACROS 11766–5000) 50.91 g of $H_2O$ and 46.80 of ethanol (Quantum Chemical, Newark N.J.) were mixed. The alkoxide solution containing the phosphoric acid was slowly added to the aqueous solution containing the dodecylamine. A dark gelatinous material formed. Calcination proceeded at 500° C. for 4 hrs in air. The material was pelletized, as described above, for microreactor evaluations.

Example 5

Preparation of 5 mole % V. 5 mole % Sb. in silica containing matrix

In one container. 0.33 g of vanadium tri-ispropoxide (Aldrich 25,308-1), 4.03 g of TEOS (E85947-87), 0.36 g of Sb(III) n-butoxide, 4.01 g of dodecylamine (ACROS 11766–5000) was added. Into an addition funnel, 42.53 g of water was added. The water slowly added to the alkoxide solution. Reaction proceeded almost immediately, and a gelatinous material formed following addition. Calcination proceeded at 500° C. for 4 hrs in air. The material was pelletized, as described above, for microreactor evaluations.

Example 6

Preparation of 10 mole % V in tantalum containing matrix

Into a dropping funnel, 20.31 g of tantalum ethoxide (Aldrich, 33.911-3) and 1.14 vanadium tri-isopropoxide (Johnson-Matthey 89798) were added. In a separate container, 1.25 g of dodecylamine (Acros, 320961), 10.205 g of ethanol (Johnson Matthey, AX0441-6) and 13.32 ml of water were added and dispersed with sonication. The alkoxide solution was slowly added to the solution containing the dodecylamine and water. Sonication continued throughout this addition. The final temperature of the solution was 80° C. The final pH=4.55. Reaction proceeded immediately upon addition. A gelatinous material formed. The material was calcined at 300° C. for 4 hours in air.

Sample preparation for the microreactors proceeded as described above. The powders were pelletized to 20.000 psi into small disks, which were subsequently granulated on −40, +60 mesh screens for microreactor evaluations.

EXAMPLE 7

Preparation of 5 mole % V in tantalum matrix

Into a dropping funnel, 20.31 g of tantalum ethoxide (Aldrich 33,911-3) and 0.56 vanadium tri-isopropoxide (JM 89798) were added. Into a separate container. 1.25 g of dodecylamine (Acros, 320961), 10.205 g of ethanol (JM. AX0441-6) and 13.32 ml of water were added and dispersed with sonication. The alkoxide solution was slowly added to the solution containing the dodecylamine and water. Sonication continued throughout this addition. The final temperature of the solution was 75° C. The final pH=5.01. Hydrolysis/precipitation proceeded immediately upon addition. A gelatinous, cloudy material formed. The material was calcined at 300° C. for 4 hours in air. Sample preparation for the microreactors proceeded as describe above.

Example 8

Preparation of 5 mole % V in a niobium oxide matrix

A procedure similar to that described in Example 1 was used. 15.9 g of niobium ethoxide (Alfa, 14689) was added to 0.36 g of vanadium trisisopropoxide (Johnsom Matthey, 89798) in an inert atmosphere drybox. The material was loaded into a dropping funnel. In a separate container, 1.75 g of dodecylamine (Acros), 0.13 g of 37 wt % HCI solution, and 16.23 g of water were combined with 1.65 ml of ethanol (Quantum Chemicals, punctilious). The solution containing the alkoxides was slowly added to the aqueous solution containing the dodecylamine. A white, gelatinous material formed almost immediately. The material was calcined in air at 300° C. for 4 hours. Catalysts were formed for microreactor evaluations by pelletizing at 20,000 psi to form small disks which are subsequently crushed and sieved. For fixed bed reactor evaluations −40. +60 mesh screens were used.

Example 9

Preparation of 1 mole % V in a niobium oxide matrix

An identical procedure (as described directly above) was used, adjusting for the different cation stoichiometry. Hence, 15.9 g of niobium ethoxide was combined with 0.072 g of vanadium tris-isoproppoxide. The material was calcined in air at 300° C. for 4 hours.

TABLE 1

Catalyst Performance

| Catalyst | $k(sec^{-1})$ (temp evaluation) | % furan selectivity at 40% conv. selectivity | % maleic anhydride at 40% conv |
|---|---|---|---|
| VPO (control) | 0.39 (300° C.) | 7 | 11 |
| Example 1 | 3.81 (300° C.) | 15 | 5 |
|  | 0.367 (250° C.) | 12 | 6 |
| Example 2 | not determined (high activity at 297° C.) | — | — |
| Example 3 | not determined (high activity at 293° C.; 100% conversion under all conditions)) | — | — |
| Example 4 | 1.5 (301° C.) | 8 | 12 |
| Example 5 | 1.24 (300° C.) | 14 | 6 |
| Example 6 | 0.19 (300° C.) | 3 (at 20% conversion) | 2 (at 20% conversion) |
| Example 7 | 0.092 (300° C.) | — | — |
| Example 8 | 0.134 (300° C.) | 3 (at 20% conversion) | 2 (at 20% conversion) |

TABLE 1-continued

Catalyst Performance

| Catalyst | k(sec$^{-1}$) (temp evaluation) | % furan selectivity at 40% conv. selectivity | % maleic anhydride at 40% conv |
|---|---|---|---|
| Example 9 | 0.127 (300° C.) | 4 (at 20% conversion) | 4 (at 20% conversion) |

What is claimed is:

1. A composition comprising a catalytic species dispersed in and distributed throughout a sol-gel route prepared substrate having a small pore size, prior to calcination, wherein the catalytic species is selected from the group consisting of vanadium oxides, vanadium phosphorous oxides and vanadium antimony oxides, wherein the sol-gel route prepared substrate is selected from the group consisting of silicon, titanium, tantalum and niobium oxides, provided that when the sol-gel route prepared substrate is silicon oxide, the catalytic species is not vanadium oxide and wherein the composition is prepared via a sol-gel process in the presence of an organic directing group.

2. The composition of claim 1 wherein the organic directing group is dodecylamine.

3. In a process for the oxidation of butadiene to furan and maleic anhydride, an improvement comprising the use of a catalyst comprising catalytic species dispersed in and distributed throughout a sol-gel route prepared substrate having a small pore size, prior to calcination, wherein the catalytic species is selected from the group consisting of vanadium oxides, vanadium phosphorous oxides and vanadium antimony oxides, wherein the sol-gel route prepared substrate is selected from the group consisting of silicon, titanium, tantalum and niobium oxides, provided that when the sol-gel route prepared substrate is silicon oxide, the catalytic species is not vanadium oxide and wherein the composition is prepared via a sol-gel process in the presence of an organic directing group.

4. The process of claim 3 wherein the organic directing group is dodecylamine.

* * * * *